United States Patent [19]
Takamizawa et al.

[11] 4,089,882
[45] May 16, 1978

[54] METHOD OF PREPARING FLUOROALKYL-CONTAINING ORGANOSILANES

[75] Inventors: Minoru Takamizawa; Mitsuo Umemura; Kazuo Kooya, all of Annaka, Japan

[73] Assignee: Shin-Etsu Chemical Co., Ltd., Tokyo, Japan

[21] Appl. No.: 812,855

[22] Filed: Jul. 5, 1977

Related U.S. Application Data

[63] Continuation of Ser. No. 560,107, Mar. 19, 1975.

[30] Foreign Application Priority Data

Mar. 22, 1974 Japan .................................. 49-32314

[51] Int. Cl.$^2$ .............................................. C07F 7/08
[52] U.S. Cl. .............................................. 260/448.2 E
[58] Field of Search .................................. 260/448.2 E

[56] References Cited

U.S. PATENT DOCUMENTS

| | | | |
|---|---|---|---|
| 2,721,873 | 10/1955 | MacKenzie et al. | 260/448.2 E |
| 2,823,218 | 2/1958 | Speier et al. | 260/448.2 E |

*Primary Examiner*—Paul F. Shaver
*Attorney, Agent, or Firm*—Toren, McGeady and Stanger

[57] ABSTRACT

Fluoroalkylsilanes of the general formula $R'CH_2CH_2SiR_nX_{3-n}$ are prepared by reaction of an organohydrogensilane of the general formula $R_nSiHX_{3-n}$ with a fluoroolefin of the general formula $R'CH=CH_2$, where R is an alkyl or aryl group, R' is a perfluoroalkyl group, X is a halogen atom or an alkoxy group and $n$ is 0, 1 or 2 in the presence of a binary catalyst composed of a platinum compound and stannous chloride under relatively mild conditions of temperature and pressure, at a very high yield.

14 Claims, No Drawings

METHOD OF PREPARING FLUOROALKYL-CONTAINING ORGANOSILANES

This is a continuation of application Ser. No. 560,107 filed Mar. 19, 1975.

FIELD OF THE INVENTION

This invention relates to a method for the preparation of flouroalkyl-containing organosilanes, in which the fuloroalkyl group is bonded to a silicon atom.

DESCRIPTION OF THE PRIOR ART

A prior art method for the preparation of fluoroalkylsilanes by reaction of an alkylsilane with an olefin having a perfuloroalkyl group have employed an organic peroxide as the reaction catalyst, as described in the paper presented by E. T. McBee et al. in Journal of the American Chemical Society, 79, 2329 (1957). The method is disadvantaged by the fact that the perfuloroalkyl group has a strong electron-attractive effect, imparting a very low reactivity to the olefin compared to the case with an olefin having no perfuloroalkyl group and, for that reason, the reaction should be carried out at high temperature and pressure.

In another method known for the preparation of the silanes of the kind, an alkylhydrogenchlorosilane and an olefin having a perfluoroalkyl group are reacted at a temperature between 150° and 300° C in the presence of a platinum catalyst, as described in British Specification 809,317 and in the paper presented by P. Tarrant in Journal of the Americal Chemical Society, 77, 6536 (1957). This method is also disadvantaged not only by a low yield of the silane product and a very great amount of such by-products as undesired silanes and telomers and polymers of the olefin but also by complexity in the design of the reaction apparatus as well as difficulties in the operation due to a very high spontaneous reaction pressure of, say, from 20 to 40 atmospheres, at the above-mentioned reaction temperature. Therefore, the commercial production of the silanes according to the prior art method is uneconomical in respect of equipment and operational costs.

OBJECTS OF THE INVENTION

It is a general object of this invention to provide a method for preparing fluoroalkyl-containing organosilanes which is free of the above-described disadvantages. A further object of the invention is to provide a method for preparing the silanes of the kind in which the pertinent reaction is carried out under relatively mild conditions of temperature and pressure with a very high yield.

SUMMARY OF THE INVENTION

The method of the invention comprises reacting an organohydrogensilane represented by the general formula

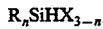   (I)

where R is an alkyl or aryl group, X is a halogen atom or an alkoxy group and $n$ is 0, 1 or 2, with a fluorinated olefin represented by the general formula
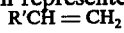   (II)

where R' is a perfluoroalkyl group having 1 to 5 carbon atoms in the presence of a binary catalyst composed of a platinum compound and stannous chloride, to produce fluoroalkylsilane having the general formula $R'CH_2CH_2SiR_nX_{3-n}$ where R',R,$n$ and X are the same as defined above.

DETAILED DESCRIPTION OF THE INVENTION

This invention is based on the discovery that in the method for the preparation of the fluoroalkyl-containing organosilanes by reaction of an organohydrogensilane of formula (I) with a fluorinated olefin of formula (II), a binary catalyst composed of a platinum compound and stannous chloride can exhibit remarkable effects on the reaction with very high conversion and yield at and under relatively low temperature and pressure, and that by use of the binary catalyst any undesired by-products, such as different silanes and telomers and polymers of the olefin can remarkably be reduced.

Speaking of the organohydrogensilane as one of the starting materials represented by formula (I), the alkyl group as denoted by R is exemplified by methyl, ethyl, propyl and butyl groups while the aryl group as the alternative for the above alkyl group is exemplified by a phenyl group; the halogen atom as denoted by X is exemplified by chlorine and bromine, while the alkoxy group as the alternative for the above halogen atom is exemplified by methoxy, ethoxy and propoxy group. Such organohydrogensilanes include trichlorosilane, methyldichlorosilane, dimethylchlorosilane, methyldimethoxysilane, phenyldichlorosilane, phenylmethylchlorosilane, phenyldiethoxysilane and phenyldimethoxysilane.

Next, speaking of the fluorinated olefin as the other starting material represented by formula (II), reacting with the organohydrogensilane, the perfluoroalkyl group as denoted by R' has 1 to 5 carbon atoms and is exemplified by trifluoromethyl, pentafluoroethyl, heptafluoropropyl and undecarfluoropentyl groups. The olefins include 3,3,3-trifluoropropene, 3,3,4,4,4-pentafluorobutene and 3,3,4,4-5,5,5-heptafluoropentene.

Illustrative of the binary catalysts used according to the method of the invention are mixtues of stannous chloride with chloroplatinic acid, a chloroplatinic acid-olefin complex or with such chloroplatinic acid modified with alcohols as disclosed in U.S. Pat. No. 3,220,972 and the complexes of stannous chloride and a platinum compound as disclosed in Journal of the American Chemical Society, Vol. 85, page 1691 (1963); Vol. 87, page 658 (1965) and Vol. 89, page 1592 (1967) and in U.S. Pat. No. 2,876,254.

The binary catalyst is composed of the platinum compound and the stannous chloride mixed at the ratio of 0.5 to 2 moles of tin atoms per mole of platinum atoms, or preferably in an equimolar amount so that its highest catalytic activities can be achieved.

In carrying out the method of the present invention, the above-described silane and binary catalyst are charged in a reaction vessel and kept at a predetermined temperature followed by the addition of the above-described olefin to react with the silane. In this case, the mixing ratio of the silane to the olefin on a molar basis should be within the range from 0.5 to 1.5. It is advantageous from the economical point of view, however, to set forth the molar ratio within the range from 1.0 to 1.5, if taking into account the cheapness of the silane compared to the olefin, though a lower ratio leads to a higher conversion The binary catalyst should be used in an amount such that the number of the platinum atoms contained therein is in the range from $10^{-4}$ to $10^{-6}\%$ of the number of the silicon atoms contained in the silane.

The reaction in the method of the invention is carried out at a temperature from room temperature to 100° C and under a pressure from atmospheric to 10 atmospheres.

Additionally, a solvent or solvents inactive to the silane and the olefin may optionally used, for the usual practice is done in the absence of any solvents.

The following examples illustrate the present invention.

EXAMPLE 1.

A mixture of 200 g of methyldichlorosilane and a binary catalyst prepared by mixing in a 1 : 1 volume ratio an isopropanol solution of choloroplatinic acid hexahydrate (0.01 mole Pt/1) and an isopropanol solution of stannous chloride dihydrate (0.01 mole Sn/1) in an amunt such that the platinum compound was present in $10^{-5}$ mole % of the silane was charged into a stainless steel autoclave of 1-liter volume, which had been connected through a valve to a pressurized container of 500 ml volume filled with 200 g of 3,3,3-trifluoropropene. The autoclave was closed, and the temperature was raised to and kept at 50° C. The gaseous 3,3,3-trifluoropropene was transferred into the autoclave by opening the valve while the pressure inside the autoclave was maintained at 5 atmospheres. The reaction was complete in 3 hours. The consumption of the 3,3,3-trifluoropropene was 175 g and the resulting reaction product was 365 g. The composition of the reaction product is shown below.

| | | |
|---|---|---|
| 3,3,3-Trifluoropropylmethyldichlorosilane | 93.6% | by weight |
| Methyldichlorosilane | 0.8% | " |
| 3,3,3-Trifluoropropene | 3.1% | " |
| Methyltrichlorosilane as by-product | 0.6% | " |
| High-boiling by-products | 0.9% | " |
| Other by-products (low-boiling) | 1.0% | " |

The yield of 3,3,3-trifluoropropylmethyldichlorosilane (Boiling point: 121° C; Refractive index $n_{25}^D$: 1.261) against the methyldichlorosilane consumed was 94.5% of the theoretical and the conversion of the charged methyldichlorosilane to 3,3,3-trifluoropropylmethyldichlorosilane was 93.1%.

EXAMPLE 2.

Into a four-necked flask equipped with a reflux condenser, a thermometer, a stirrer and a gas inlet tube were put 115 g of methyldichlorosilane and the same binary catalyst as used in Example 1 in an amount such that the platinum compound was present in $10^{-5}$ mole% of methyldichlorosilane. The reaction mixture was heated at 38° to 42° C under reflux with agitation, while 58 g of 3,3,3-trifluoropropene was slowly introduced through the gas inlet tube and allowed to react over a period of 12 hours under atmospheric pressure. The conversion of the methyldichlorosilane to 3,3,3-trifluoropropylmethydichlorosilane thus obtained was 72%.

EXAMPLE 3.

Into a reaction vessel were put 200 g of methyldichlorosilane and the same amount of the same binary catalyst as in Example 1, followed by the addition of 242 g of 3,3,4,4-pentafluorobutene. After the completion of the reaction at 70° C under 6 atmospheres, the reaction product was subjected to distillation to produce 3,3,4,4,4-pentafluorobutylmethyldichlorosilane (Boiling point: 130° C) at the yield 91% of the theoretical.

EXAMPLE 4.

The procedure of Example 3 was substantially repeated substituting 3,3,4,4,5,5,5-heptafluoropentene for the 3,3,4,4-pentafluorobutene used as the fluorinated olfin. The resulting reaction product was subjected to distillation to produce 3,3,4,4,5,5,5-heptafluoropentylmethyldichlorosilane (Boiling point: 137°–139° C) at the yield 90% of the theoretical.

EXAMPLE 5.

The procedure of Example 1 was substantially repeated substituting trichlorosilane for the methyldichlorosilane used as the starting silane. The yield of the 3,3,3-trifluoropropyltrichlorosilane thus produced (Boiling point: 113° C) was 95% of the theoretical.

EXAMPLE 6.

The procedure of Example 1 was substantially repeated substituting methyldimethoxysilane for the methyldichlorosilane used as the starting silane. The yield of the 3,3,3-trifluoropropylmethyldimethoxysilane thus produced (Boiling point: 72° C/100 mmHg) was 95% of the theoretical.

EXAMPLE 7.

The procedure of Example 1 was repeated with the exceptions that 265.5 g of phenyldichlorosilane was used as the starting silane in place of 200 g of the methyldichlorosilane used therein and that the reaction temperature was 80° C instead of 50° C. The yield of the 3,3,3-trifluoropropylphenyldichlorosilane thus produced (Boiling point: 98° to 100° C/10 mmHg) was 83% of the theoretical.

EXAMPLE 8.

This is a control example.

A mixture consisting of 200 g of methyldichlorosilane, 167 g of 3,3,3-trifluoropropene and 0.5 g of platinum catalyst borne on carbon (platinum content: 5% by weight) was put into a stainless steel autoclave and heated at 250° C for 9 hours, to produce 360 g of a reaction product. The maximum of the pressure inside the autoclave during the reaction was 40 atmospheres. The composition of the reaction product is shown in the following.

| | | |
|---|---|---|
| 3,3,3-Trifluoropropylmethyldichlorosilane | 70.1% | by weight |
| Methyldichlorosilane | 8.8% | " |
| 3,3,3-Trifluoropropene | 6.2% | " |
| Methyltrichlorosilane as by-product | 4.7% | " |
| High-boiling by-products | 8.1% | " |
| Other by-products (low-boiling) | 2.1% | " |

The yield of 3,3,3-trifluoropropylmethyldichlorosilane against the methyldichlorosilane consumed was 81.8% of the theoretical and the conversion of the charged methyldichlorosilane to 3,3,3-trifluoropropylmethyldichlorosilane was 68.8%.

What we claim is:

1. In a method for preparing a fluoroalkylsilane represented by the general formula
$$R'CH_2CH_2SiR_nX_{3-n}$$

where R' is a perfluoroalkyl group having 1 to 6 carbon atoms, R is an alkyl or aryl group, X is a halogen atom or an alkoxy group and $n$ is 0, 1 or 2, by reacting an organohydrogensilane represented by the general formula $R_nSiHX_{3-n}$ where R, X and $n$ are the same as defined above with a fluorinated olefin represented by the general formula $R'CH=CH_2$ where R' is the same as defined above, the improvement which comprises carrying out the reaction in the presence of a binary catalyst composed of a platinum compound selected from the group consisting of chloroplatinic acid, chloroplatinic acid-olefin complexes and chloroplatinic acid modified with alcohols and stannous chloride.

2. The method as claimed in claim 1 wherein said binary catalyst is composed of the platinum compound and the stannous chloride at the ratio of from 0.5 to 2 moles of tin atoms per mole of platinum atoms.

3. The method as claimed in claim 1 wherein said binary catalyst is present in an amount such that the molar ratio of the platinum atoms in said platinum compound to the silicon atoms in said organohydrogensilane is from $10^{-4}$ to $10^{-6}\%$.

4. The method as claimed in claim 1 wherein said organohydrogensilane is selected from the group consisting of trichlorosilane, methyldichlorosilane, dimethylchlorosilane, methyldimethoxysilane, phenyldichlorosilane, phenylmethylchlorosilane, phenyldiethoxysilane and phenyldimethoxysilane.

5. The method as claimed in claim 1 wherein said fluorinated olefin is selected from the group consisting of 3,3,3-trifluoropropene, 3,3,4,4,4-pentafluorobutene and 3,3,4,4,5,5,5-heptafluoropentene.

6. The method as claimed in claim 1 wherein said organohydrogensilane and said fluorinated olefin are present at the ratio on a molar basis of the former to the latter within the range from 0.5 to 1.5.

7. The method as claimed in claim 1 wherein said organohydrogensilane is reacted with said fluorinated olefin at a temperature from room temperature to 100° C.

8. The method as claimed in claim 1 wherein said organohydrogensilane is reacted with said fluorinated olefin under a pressure from atmospheric pressure to 10 atmospheres.

9. The method as claimed in claim 1 wherein said fluoroalkylsilane is 3,3,3-trifluoropropylmethyldichlorosilane.

10. The method as claimed in claim 1 wherein said fluoroalkylsilane is 3,3,4,4,4-pentafluorobutylmethyldichlorosilane.

11. The method as claimed in claim 1 wherein said fluoroalkylsilane is 3,3,4,4,5,5,5-heptafluoropentylmethyldichlorosilane.

12. The method as claimed in claim 1 wherein said fluoroalkylsilane is 3,3,3-trifluoropropyltrichlorosilane.

13. The method as claimed in claim 1 wherein said fluoroalkylsilane is 3,3,3-trifluoropropylmethyldimethoxysilane.

14. The method as claimed in claim 1 wherein said fluoroalkylsilane is 3,3,3-trifluoropropylphenyldichlorosilane.

* * * * *